(12) United States Patent
Lesso

(10) Patent No.: US 12,405,243 B2
(45) Date of Patent: Sep. 2, 2025

(54) CIRCUITRY FOR ANALYTE MEASUREMENT

(71) Applicant: Cirrus Logic International Semiconductor Ltd., Edinburgh (GB)

(72) Inventor: John P. Lesso, Edinburgh (GB)

(73) Assignee: Cirrus Logic Inc., Austin, TX (US)

(*) Notice: Subject to any disclaimer, the term of this patent is extended or adjusted under 35 U.S.C. 154(b) by 299 days.

(21) Appl. No.: 17/940,225

(22) Filed: Sep. 8, 2022

(65) Prior Publication Data

US 2024/0085370 A1   Mar. 14, 2024

(51) Int. Cl.
*G01N 27/416* (2006.01)
*G01N 27/00* (2006.01)
*G01N 27/30* (2006.01)

(52) U.S. Cl.
CPC ....... *G01N 27/4161* (2013.01); *G01N 27/002* (2013.01); *G01N 27/30* (2013.01)

(58) Field of Classification Search
CPC .. G01N 27/4161; G01N 27/002; G01N 27/30; G01N 27/48; G01N 27/4163; G01R 31/2829
USPC .......................................................... 324/74
See application file for complete search history.

(56) References Cited

U.S. PATENT DOCUMENTS

| | | | |
|---|---|---|---|
| 5,352,349 A * | 10/1994 | Inamoto .................. | C12Q 1/001 204/402 |
| 6,447,659 B1 * | 9/2002 | Peng ................... | G01N 27/4045 204/402 |
| 8,773,106 B2 * | 7/2014 | Elder .................. | G01N 27/3274 702/19 |
| 9,398,882 B2 * | 7/2016 | Stafford ............... | A61B 5/6849 |
| 9,451,908 B2 * | 9/2016 | Kamath ............... | A61B 5/1473 |
| 11,399,745 B2 * | 8/2022 | Simpson ............... | A61B 5/1486 |
| 11,633,133 B2 * | 4/2023 | Brister ................... | A61B 5/742 600/347 |
| 2005/0161346 A1 * | 7/2005 | Simpson ............ | G01N 27/3274 205/792 |
| 2013/0123596 A1 * | 5/2013 | Kamath ............. | A61B 5/14865 600/347 |
| 2018/0156605 A1 * | 6/2018 | Swallow ................ | G01N 29/00 |
| 2018/0323750 A1 | 11/2018 | Wang et al. | |
| 2021/0382045 A1 | 12/2021 | Aran et al. | |

OTHER PUBLICATIONS

International Search Report and Written Opinion of the International Searching Authority, International Application No. PCT/GB2023/052195, mailed Nov. 3, 2023.

* cited by examiner

*Primary Examiner* — Christopher P McAndrew
(74) *Attorney, Agent, or Firm* — Jackson Walker L.L.P.

(57) ABSTRACT

Circuitry for measuring a characteristic of an electrochemical cell, the electrochemical cell comprising at least one working electrode and a counter electrode, the circuitry comprising: driver circuitry configured to apply a working bias voltage to the at least one working electrode and a counter bias voltage at the counter electrode to produce a first voltage bias between the at least one working electrode and the counter electrode; control circuitry configured to adjust the first voltage bias over a first bias range by varying the working bias voltage and the counter bias voltage.

20 Claims, 11 Drawing Sheets

CIRCUITRY FOR ANALYTE MEASUREMENT

TECHNICAL FIELD

The present disclosure relates to circuitry for measuring characteristics in electrochemical sensors.

BACKGROUND

Electrochemical sensors are widely used for the detection of one or more particular chemical species, analytes, as an oxidation or reduction current. Such sensors comprise an electrochemical cell, consisting of two or more electrodes configured for contact with an analyte whose concentration is to be ascertained. Such sensors also comprise circuitry for driving one or more of the electrodes and for measuring a response at one or more of the electrodes.

Depending on the analyte being analysed, it may be desirable to bias an electrochemical cell with either a positive bias or a negative bias. Typically, this is achieved for a two-electrode sensor by holding one electrode (e.g. a working electrode) of the cell at a fixed voltage (such as half the supply voltage) and applying a bias voltage at another electrode (e.g., a counter electrode) of the cell, or vice versa. To support biasing of the cell to +/−V, a minimum supply voltage of 2V is required. When electrochemical sensors are battery powered, for example when used in continuous glucose monitoring, the output voltage of the battery used may not be sufficient to support the swing in bias needed for some applications.

SUMMARY

Embodiments of the disclosure aim to address or at least ameliorate one or more of the above issues by adjusting the voltage applied to two electrodes of an electrochemical cell.

According to a first aspect of the disclosure, there is provided circuitry for measuring a characteristic of an electrochemical cell, the electrochemical cell comprising at least one working electrode and a counter electrode, the circuitry comprising: driver circuitry configured to apply a working bias voltage to the at least one working electrode and a counter bias voltage at the counter electrode to produce a first voltage bias between the at least one working electrode and the counter electrode; control circuitry configured to adjust the first voltage bias over a first bias range by varying the working bias voltage and the counter bias voltage.

The control circuitry may be configured to hold the working bias voltage at a fixed midpoint voltage while varying the counter bias voltage between a lower reference voltage and an upper reference voltage of the driver circuitry.

The lower reference voltage may be a ground reference voltage of the driver circuitry positively offset by a headroom voltage. The upper reference voltage may be a supply voltage of the driver circuitry negatively offset by the headroom voltage.

When the first voltage bias is a negative voltage bias, the control circuitry may be configured to increase a magnitude of the negative voltage bias by decreasing the counter bias voltage until the counter bias voltage is substantially equal to the lower reference voltage.

When the counter bias voltage reaches the lower reference voltage, the control circuitry may be configured to increase the working bias voltage to further increase the magnitude of the negative voltage bias.

When the first voltage bias is a positive voltage bias, the control circuitry may be configured to increase a magnitude of the positive voltage bias by increasing the counter bias voltage until the counter bias voltage is substantially equal to the upper reference voltage.

Circuitry of claim 6, wherein, when the counter bias voltage reaches the upper reference voltage, the control circuitry may be configured to decrease the working bias voltage to further increase the magnitude of the positive voltage bias.

The first bias range may be between a negative bias voltage and a positive bias voltage.

During a first time period, the control circuitry may be configured to linearly increase the first voltage bias from the negative bias voltage to the positive bias voltage. During a second time period, the control circuitry may be configured to linearly decrease the first voltage bias from the positive bias voltage to the negative bias voltage.

The first voltage bias may be modulated by a square wave.

The voltage bias may be modulated by modulating the working bias voltage and/or the counter bias voltage.

The circuitry may comprise a transimpedance amplifier (TIA) comprising: a first input coupled to the working electrode; a second input configured to receive the working bias voltage; an output configured to output an output voltage; and a feedback resistor coupled between the output and the first input.

The control circuitry may be configured to vary a resistance of the feedback resistor in dependence the working bias voltage.

The circuitry may comprise a current source configured to provide an offset current to the first input.

The circuitry may further comprise an analog-to-digital converter configured to convert the output voltage into a digital representation of the output voltage.

The at least one working electrode may comprise a first working electrode and a second working electrode.

The working bias voltage may be applied to the first working electrode. The first voltage bias may be between the first working electrode and the counter electrode. The driver circuitry may be configured to apply a second working bias voltage to the second working electrode to produce a second voltage bias between the second working electrode and the counter electrode. The control circuitry may be configured to adjust the second voltage bias over a second bias range by varying the second working bias voltage and the counter bias voltage.

The control circuitry may be configured to adjust the working bias voltage, the second working bias voltage and the counter bias voltage such that a sum of absolute distinct values of the first voltage bias and the second voltage vias is less than a supply voltage of the driver circuitry.

According to another aspect of the disclosure, there is provided an electronic device, comprising the circuitry as described above. The device may comprise a continuous glucose monitor or other such analyte monitor.

The device may comprise one of a mobile computing device, a laptop computer, a tablet computer, a games console, a remote control device, a home automation controller or a domestic appliance, a toy, a robot, an audio player, a video player, or a mobile telephone, and a smartphone.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

BRIEF DESCRIPTION OF DRAWINGS

Embodiments of the present disclosure will now be described by way of non-limiting examples with reference to the drawings, in which.

DESCRIPTION OF EMBODIMENTS

Figure 1:
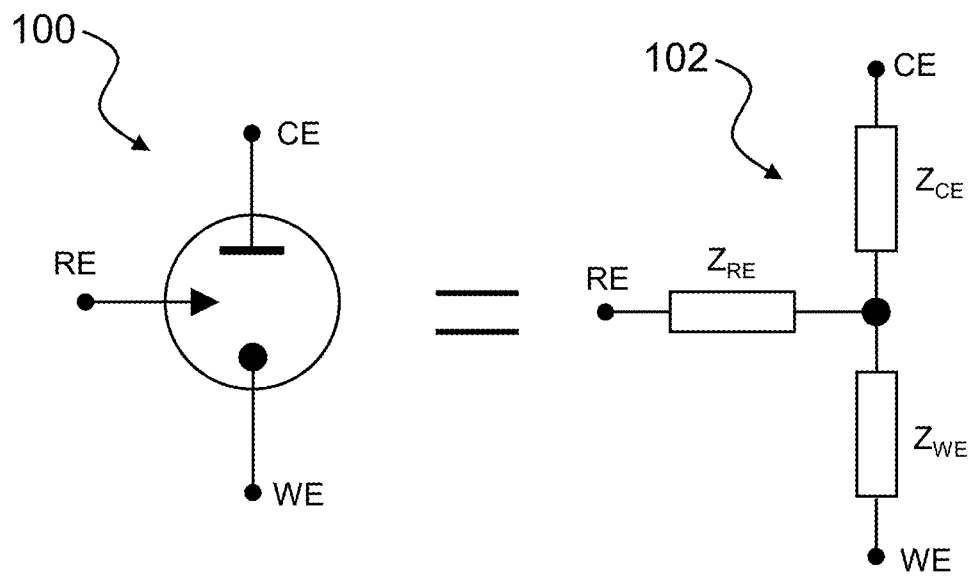
FIG. 1 illustrates a schematic diagram and electrical equivalent circuit for a three-electrode electrochemical cell.

FIG. 1 is a schematic diagram of an electrochemical cell 100 comprising three electrodes, namely a counter electrode CE, a working electrode WE and a reference electrode RE. FIG. 1 also shows an equivalent circuit 102 for the electrochemical cell comprising a counter electrode impedance ZCE, a working electrode impedance ZWE and a reference electrode impedance ZRE.

To determine a characteristic of the electrochemical cell, and therefore an analyte concentration, a bias voltage is applied at the counter electrode CE and a current at the working electrode is measured. The reference electrode RE is used to measure a voltage drop between the working electrode WE and the reference electrode RE. The bias voltage is then adjusted to keep the voltage drop between RE and WE constant. As the resistance in the cell 100 increases, the current measured at the working electrode WE decreases. Likewise, as the resistance in the cell 100 decreases, the current measured at the working electrode WE increases. Thus the electrochemical cell 100 reaches a state of equilibrium where the voltage drop between the reference electrode RE and the working electrode WE is maintained constant. Since the bias voltage at the counter electrode CE and the measured current at WE are known, the resistance of the cell 100 can be ascertained.

Figure 2:
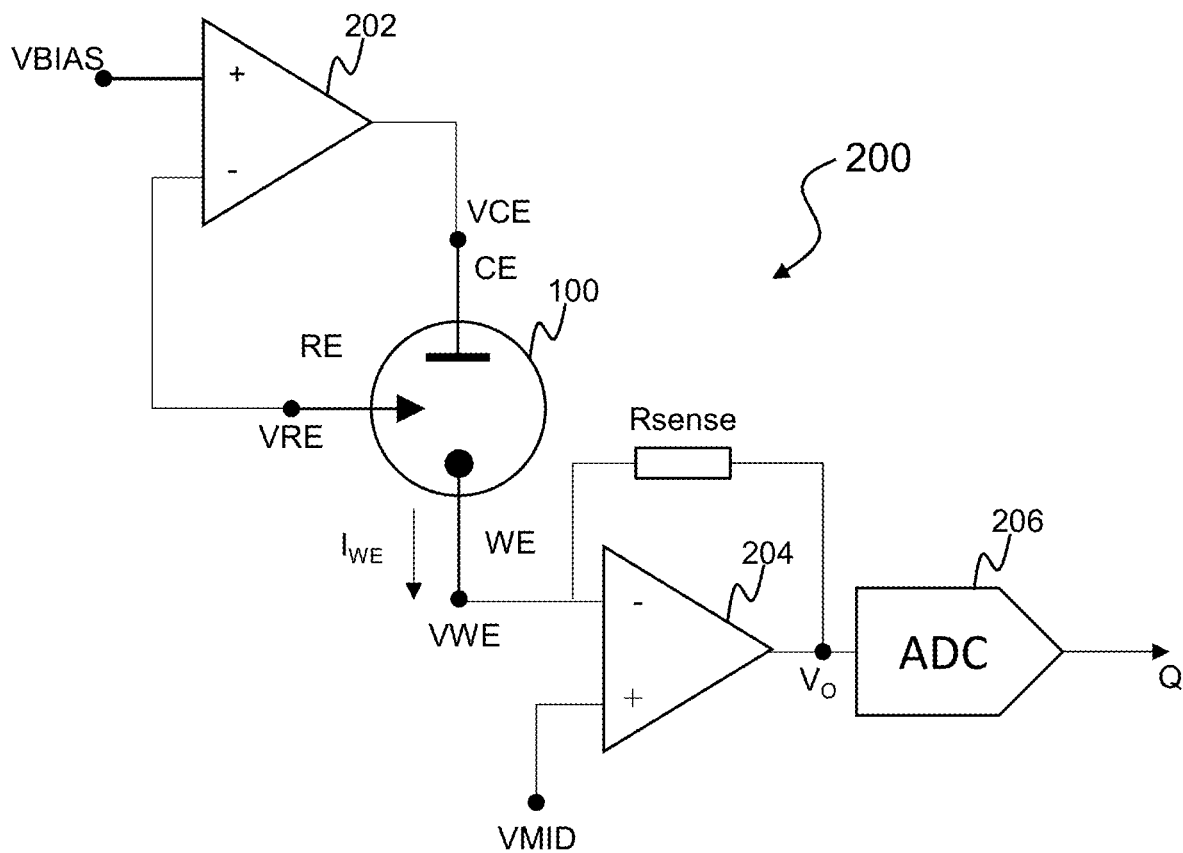
FIG. 2 is a schematic diagram of an example prior art drive and measurement circuit.

FIG. 2 illustrates an example prior art drive and measurement circuit 200 which is configured to implement the above explained cell characterisation, specifically for measuring an analyte concentration in the electrochemical cell 100 shown in FIG. 1. The circuit 200 comprises a first amplifier 202 and a second amplifier 204. Each of the first and second amplifiers 202, 204 may comprise one or more op-amps. A non-inverting input of the first amplifier 202 is coupled to a bias voltage VBIAS. An inverting input of the first amplifier 202 is coupled to the reference electrode RE. An output of the first amplifier 202 is coupled to the counter electrode CE and configured to drive the counter electrode CE with a counter electrode bias voltage VCE. The counter electrode bias voltage VCE applied at the counter electrode CE by the first amplifier 202 is proportional to the difference between the bias voltage VBIAS and the voltage VRE at the reference electrode RE. As such, the first amplifier 202 acts to maintain the voltage between the reference electrode RE and the working electrode WE at the bias voltage VBIAS. An inverting input of the second amplifier 204 is coupled to the working electrode WE and the non-inverting input of the second amplifier 204 is coupled to a fixed reference voltage, VMID. VMID is typically set to half the supply voltage of the circuit 200 (i.e., VDD/2). A feedback loop comprising a feedback resistor RF is coupled between the inverting input and an output of the second amplifier 204. As such, the second amplifier 204 may operate as a transimpedance amplifier. The second amplifier 204 is thus operable to output a voltage VO which is proportional to the current IWE at the working electrode WE. The output voltage VO is then provided to an analog-to-digital converter (ADC) 206 which outputs a digital output Q which represents the current IWE at the working electrode WE.

To bias the counter electrode CE, and therefore the electrochemical cell 100, at different voltages, the bias voltage VBIAS may be adjusted. Between ground (e.g. zero volts) and the supply voltage VDD. With the non-inverting input of the second amplifier 204 set at VDD/2, a positive bias may be applied to the cell 100 by maintaining the bias voltage VBIAS above VDD/2. Likewise, a negative bias may be applied to the cell 100 by maintaining the bias voltage VBIAS below VDD/2.

Figure 3:
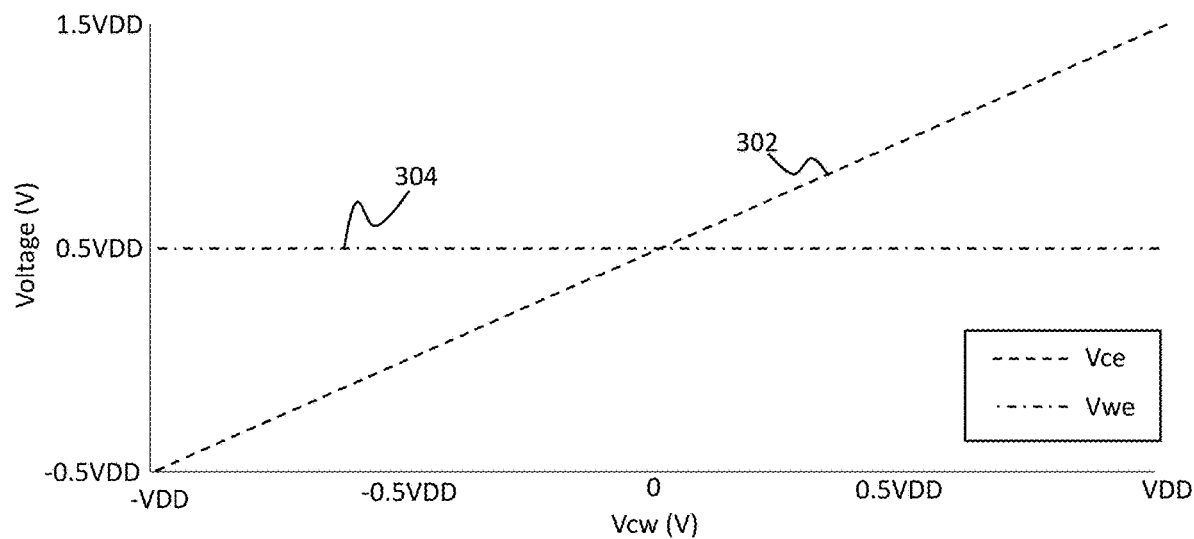
FIG. 3 is a graph showing a conventional regime for driving the cell of the measurement circuit in FIG. 2.

FIG. 3 is a graph of cell voltage drop VCW (i.e., the voltage drop VCW between the counter electrode CE and the working electrode WE) versus electrode voltage. The graph shows both the counter electrode voltage VCE, denoted by line 302, and the working electrode voltage VWE, denoted by line 304, for an example conventional bias regime. It can be seen that to achieve a swing in cell voltage drop between −VDD and +VDD when the working electrode voltage VWE is maintained substantially at VDD/2 (or 0.5 VDD), the voltage VCE at the counter electrode CE must be varied between −0.5 VDD and 1.5 VDD. Thus, a voltage greater than the VDD needs to be applied at the counter electrode CE to achieve a voltage swing of between −VDD and +VDD.

Figure 4:
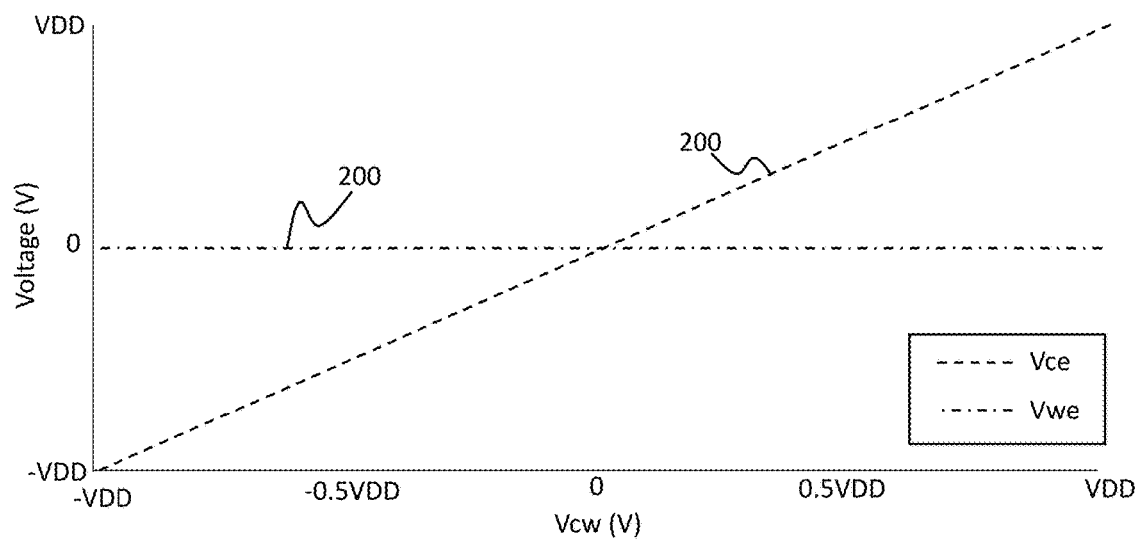
FIG. 4 is a graph showing a conventional regime for driving the cell using the measurement circuit in FIG. 2 and a voltage doubler.

Generating such a voltage swing is conventionally achieved using a voltage doubler (not shown). For example, as shown in FIG. 4, the working electrode WE may be held at ground or 0V and the voltage doubler may generate a negative voltage rail, which can be provided to the counter electrode CE. Alternatively, the voltage doubler may be used to double the supply voltage, e.g., from VDD to 2 VDD, whilst hold the working electrode at the supply voltage, e.g., VDD.

Whilst conventional voltage doubler implementations may achieve the result of extending the voltage range of the cell voltage drop VCW of the cell 100, such implementations increase power consumption and on-chip noise. In addition, since voltage doublers tend to be provided off-chip, their implementation also tends to increase pin count and off-chip component cost.

Embodiments of the disclosure aim to address or at least ameliorate one or more of the above issues by reducing the overall power and size of the drive circuitry required to measure analyte concentration in electrochemical sensors. Specifically, embodiments of the disclosure utilise a novel approach to controlling voltage drop across an electrochemical cell which substantially eliminates the requirement for voltage doublers and/or other power and space intensive circuitry, thereby reducing power consumption, size and complexity of drive circuitry.

Figure 5:
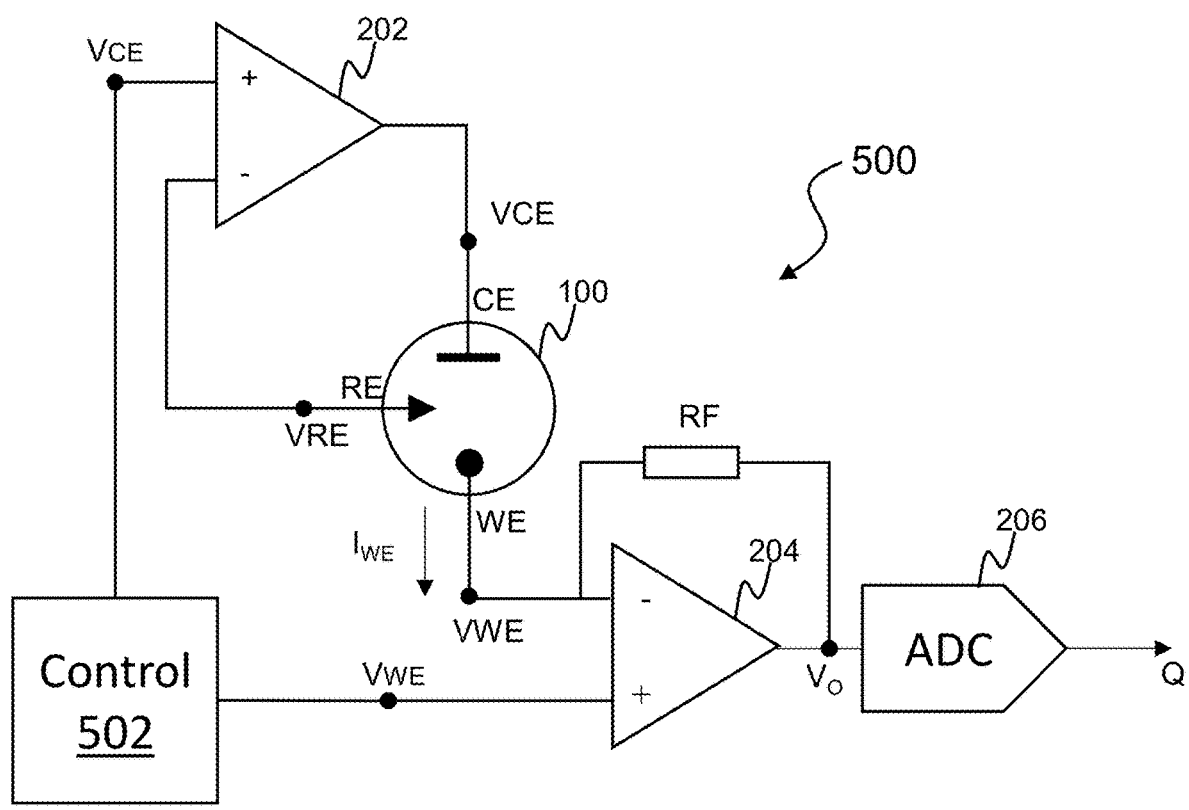
FIG. 5 is a schematic diagram of a drive and measurement circuit according to embodiments of the present disclosure.

FIG. 5 illustrates an example drive and measurement circuit 500 according to embodiments of the present disclosure. Like parts of the drive and measurement circuit 500 to the circuit 200 of FIG. 2 have been given like numerals. The circuit 500 differs from the circuit 200 of FIG. 2 in that it comprises a control module 502 configured to adjust the voltage bias VCW across the cell 100 by varying both of the working electrode bias voltage VWE and the counter electrode bias voltage VCE. In the embodiment shown, the control module 502 is configured to provide a counter electrode bias voltage VCE at the non-inverting input of the first amplifier 202 and a working electrode bias voltage VWE at the non-inverting input of the second amplifier 204. It will, however, be appreciated that in other embodiments adjustment of counter and working electrode vias voltage VCE, VWE may be achieved by other means.

By adjusting the bias voltage applied to the working electrode WE as well as that applied to the counter electrode CE, the range of values of the voltage drop VCW across the cell 100 can be increased, as will be explained in more detail below, with reference to several example control regimes.

Figure 6:
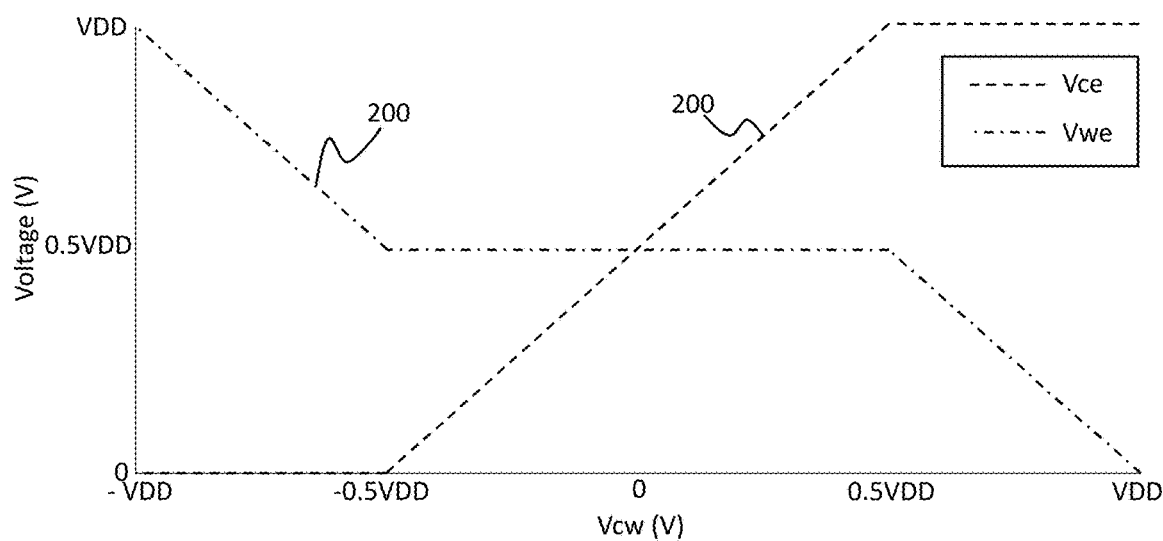
FIGS. 6 and 7 are graphs showing regimes for driving the cell of the measurement circuit in FIG. 5 according to embodiments of the present disclosure.

FIG. 6 is a graph showing a first example control regime for achieving a swing in bias voltage VCW across the cell 100 between −VDD and +VDD, where VDD is a supply voltage. When the desired voltage drop VCW across the cell is between −0.5 VDD and +0.5 VDD, the working electrode voltage VWE may be held at VMID=VDD/2 and the counter electrode voltage VCE varied between zero voltage (ground) and VDD.

When the desired voltage drop VCW increases to above 0.5 VDD, the counter electrode voltage VCE is at VDD and so cannot be increased any further (without the provision of a voltage doubler, charge pump, or similar device). As such, the counter electrode voltage VCE is maintained at VDD and the working electrode voltage VWE is decreased, thereby increasing the voltage drop VCW between the counter electrode CE and the working electrode WE. The working electrode voltage VWE can be reduced to zero volts (e.g., ground) at which point the voltage drop VCW between the counter electrode CE and the working electrode WE is VDD−0=VDD.

When the desired voltage drop VCW decreases to below 0.5 VDD, the counter electrode voltage VCE is at zero voltage (e.g., ground) and so cannot be decreased any further (without the need for a voltage doubler, charge pump, or similar device). As such, the counter electrode voltage VCE may be maintained at zero volts and the working electrode voltage VWE increased, thereby increasing the negative voltage drop VCW between the counter electrode CE and the working electrode WE. The working electrode voltage VWE can be increased to VDD at which point the voltage drop VCW between the counter electrode CE and the working electrode WE is 0−VDD=−VDD. Such a control regime may be expressed as follows:

$$V_{CE} = V_{CW} + \frac{V_{DD}}{2}$$

$$V_{WE} = V_{CE} + V_{CW}$$

Thus, by varying the voltage VWE at the working electrode WE in addition to the voltage VCE at the counter electrode CE, the voltage drop VCW across the cell 100 can be varied between +VDD and −VDD with a single supply voltage VDD (without the need for charge pumping or voltage double circuitry).

It will be appreciated in practical implementations of the circuit 500 of FIG. 5, headroom below the supply voltage VDD and above ground (0V) may be required due to limitations associated with operation of one or more components (such as the first and second amplifiers 202, 204 and any op-amps comprised therein). Such headroom may limit the range of variation of voltage drop VCW across the cell 100. Each of the counter and working electrodes CE, WE may have an upper limit of VDD−VH and a lower limit of VH, where VH is a headroom voltage. The above expressions for VCE and VWE may be updated to accommodate for this, as follows:

$$V_{CE} = \left[V_{CW} + \frac{V_{DD}}{2}\right]_{V_H}^{V_{DD}-V_H}$$

$$V_{WE} = [V_{CE} + V_{CW}]_{V_H}^{V_{DD}-V_H}$$

Figure 7:
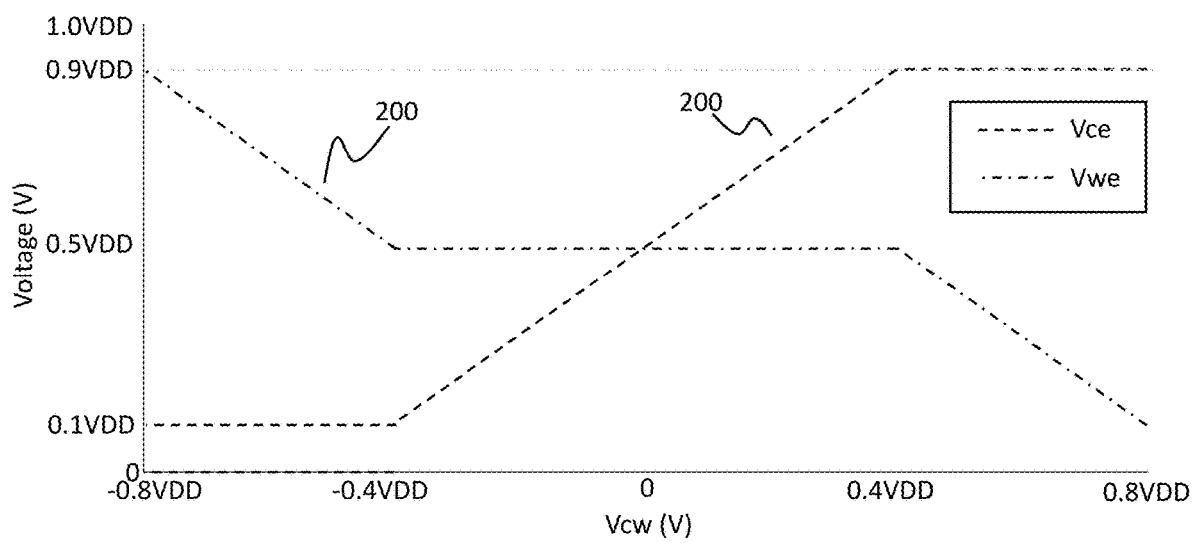

FIG. 7 is a graph showing a second example control regime which is a variation of the regime shown in FIG. 6, where a headroom voltage of 0.1 VDD is required. The counter and working electrode bias voltages VCE, VWE vary between 0.1 VDD and 0.9 VDD. As such, a swing in bias voltage VCW across the cell 100 is limited to between −0.8 VDD and +0.8 VDD, where VDD is a supply voltage. Thus, the maximum positive and negative bias VCW across the cell 100 is reduced when compared to the example shown in FIG. 6.

It will be appreciated that the cell 100 may be operated either by applying a constant voltage bias VCW across the cell 100 (for example when measuring a concentration of an analyte present in the cell 100) or by applying a varying voltage bias VCW across the cell 100 (for example when characterising or calibrating the cell 100). Such variation may include a sweep across a voltage range, known in the art as cyclic voltammetry. The inventors have realised that such cyclic voltammetry may be particularly applicable in the characterisation of aptamer-based sensors. For example, cyclic voltammetry may be used to identify cell voltage drops at which large amounts of current at generated—which may correspond to certain characteristics of analytes present in a cell, such as the cell 100.

Figure 8:
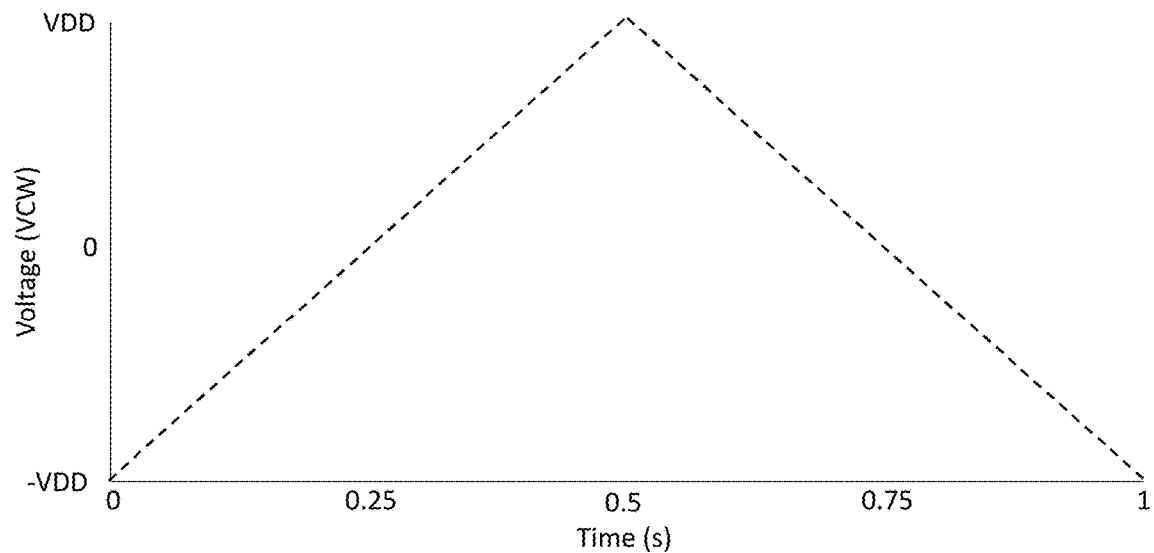
FIGS. 8 and 9 are graphs showing a cyclic voltammetry regime for driving the cell 100 of the measurement circuit in FIG. 5 according to embodiments of the present disclosure.
Figure 9:
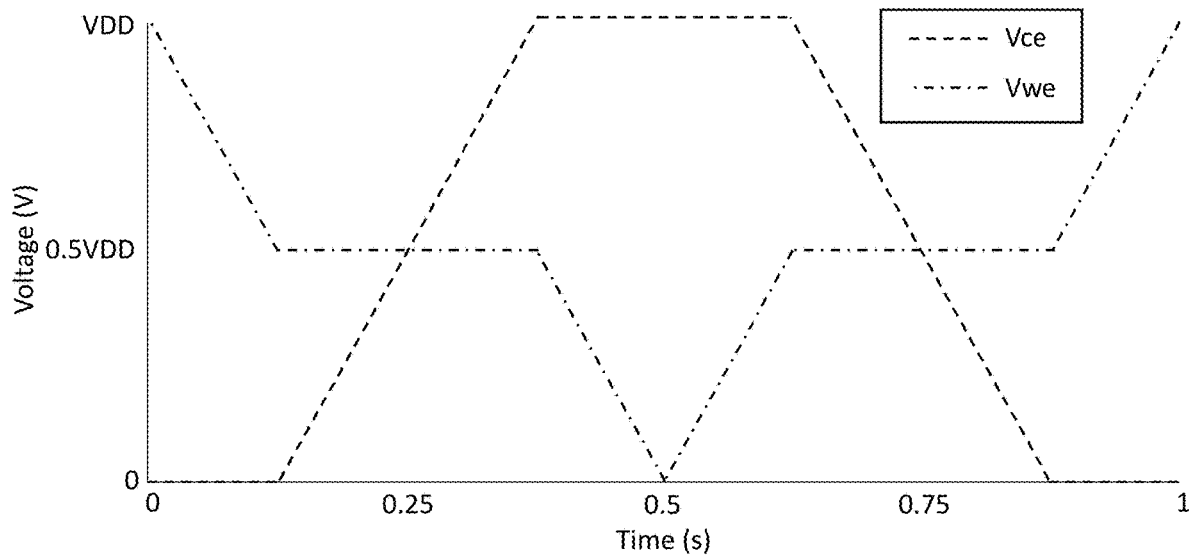

FIGS. 8 and 9 graphically illustrate an example sweep over time of the voltage drop VCW across the cell 100 from −VDD to +VDD and back to −VDD (FIG. 8) and the corresponding voltage at the counter electrode CE and working electrode WE as controlled by the control module 502 (FIG. 9).

Between 0 and 0.125 seconds, the counter electrode voltage VCE is maintained at zero volts and the working electrode voltage VWE is decreased from VDD to 0.5 VDD such that the cell voltage drop VCW increases from −VDD to −0.5 VDD. Between 0.125 seconds and 0.375 seconds, the working electrode voltage VWE is maintained at 0.5 VDD and the counter electrode voltage VCW is increased from zero volts to VDD, such that the cell voltage drop VCW increase from −0.5 VDD to 0.5 VDD. With the counter electrode voltage VCW maxed out at VDD, to continue the increase in cell voltage drop VCW, the working electrode voltage VCE is decreased between 0.375 seconds and 0.5 seconds from 0.5 VDD to zero volts (the counter electrode voltage VCE maintained at VDD). As such, the cell voltage drop VCW increases from 0.5 VDD at 0.375 seconds to VDD at 0.5 seconds.

The above described control of the counter and working electrode voltages VCE, VWE between 0 and 0.5 seconds is then reversed to sweep the cell voltage drop back down from +VDD to −VDD as shown in FIGS. 8 and 9. It will be appreciated that, in practice, the maximum achievable voltage swing may be reduced due to headroom constraints associated with circuit imperfections (as discussed above with reference to FIG. 7).

Thus, the counter and working electrode voltages VCE, VWE can be controlled by the control module 502 to sweep the voltage across the cell 100 from −VDD to +VDD and back down to −VDD. It will be appreciated that the counter and working electrode voltage VCE, VWE may be controlled to create any conceivable time-varying voltage profile across the cell 100.

It will be appreciated that it may be preferable to maintain one of the working electrode voltage VWE and the counter electrode voltage VCE constant when adjusting the other of the working and counter electrode voltages VWE, VCE. For example, maintaining one of the working and counter electrode voltages VWE, VCE constant may lead to a reduction in drive circuitry complexity as well as improving accuracy in the control of the applied bias voltage VCW across the cell 100.

Figure 10:
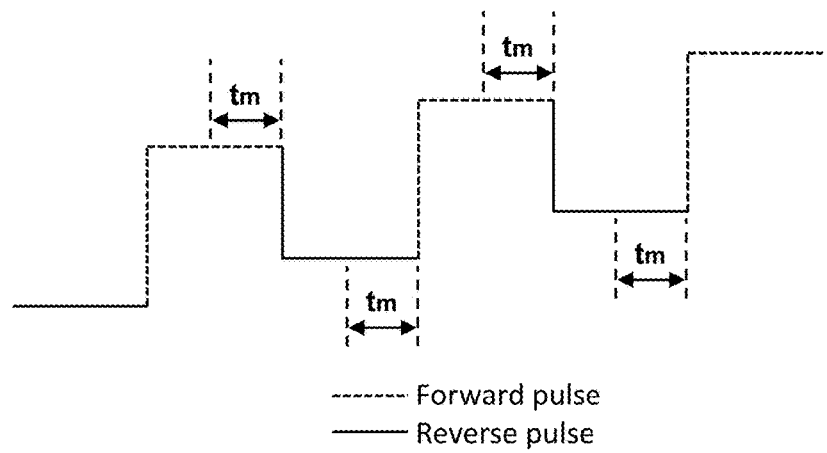
FIG. 10 is an explanatory diagram illustrating square wave voltammetry.

In various embodiments of the present disclosure, it may be preferably to modulate a varying voltage drop VCW across the cell 100 using a square wave, a sawtooth, or similar waveform. For example, the cyclic voltammetry described above may be implemented using a square wave. Such modulation is known in the art as square wave voltammetry (SWV). A linear potential sweep is combined with a square wave to generate a waveform as shown in FIG. 10.

Figure 11:
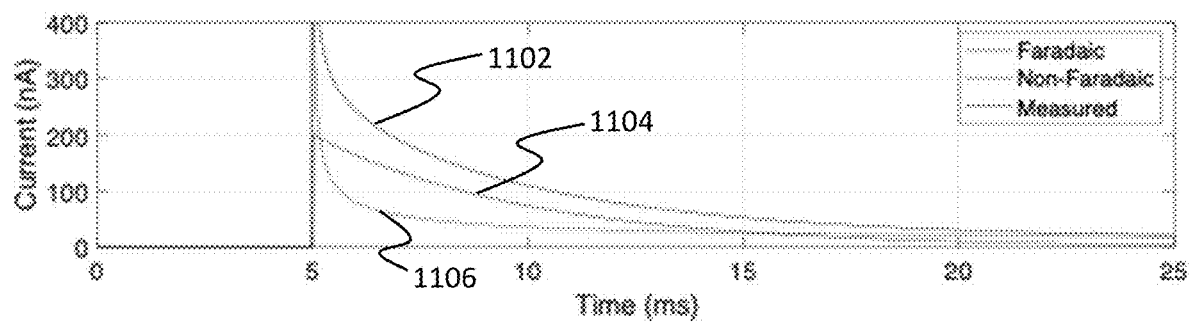
FIG. 11 is a graph of modelled current through the cell in FIG. 5 in response to a step change in voltage across the cell using the waveform shown in FIG. 10.
Figure 12:
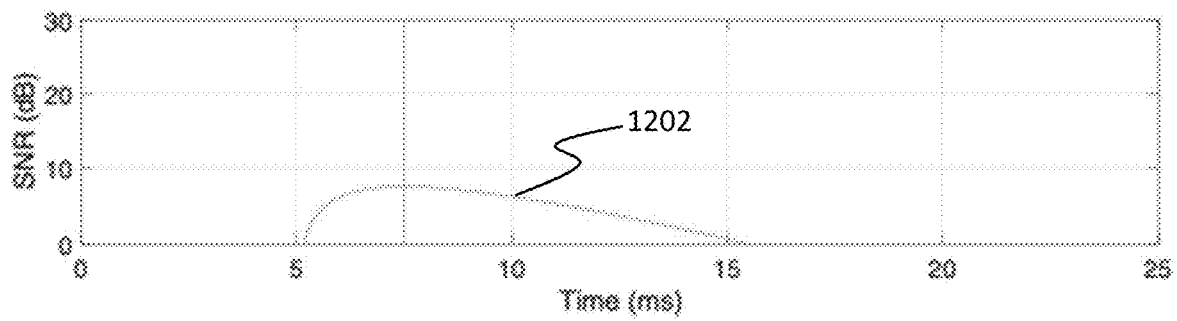
FIG. 12 is a graph of modelled signal to noise ratio of faradic vs non-faradaic current through the cell of FIG. 5.

The effect of applying such a waveform across the cell 100 will be described with reference to FIGS. 10 to 12. FIG. 10 illustrates an example square wave voltammetry waveform which may be applied across the cell 100 between the counter and working electrodes CE, WE. FIG. 11 graphically illustrates a modelled current in the cell 100 responsive to a step change in the voltage drop VCW. It can be seen that the modelled current 1102 comprises a faradaic current 1104 and a non-faradaic current 1106. The non-faradaic current 1104 is primarily due to capacitance (i.e. noise) in the system. The faradaic current 1106 is due to the chemistry of the cell 100 which we are interested in measuring. FIG. 12 graphically illustrates the signal to noise ratio (SNR) 1202 of the modelled current 1102 over time. This SNR 1202 is calculated as a ratio of the faradaic current 1106 to the non-faradaic current 1104 of the modelled current 1102.

Application of a square wave to the cell 100 substantially increases the faradaic component of current in the cell 100. However, it can be seen from FIGS. 11 and 12 that the step change in voltage drop VCW across the cell 100 leads to a surge in non-faradaic (capacitive) current which dwarfs the faradaic current. As such, as shown in FIG. 10, the current flowing through the cell 100 is preferably measured during time tm, after 15 ms in the example shown in FIGS. 11 and 12. In doing so, the non-faradaic component 1104 of the measured current falls below the faradaic component 1106.

Figure 13:
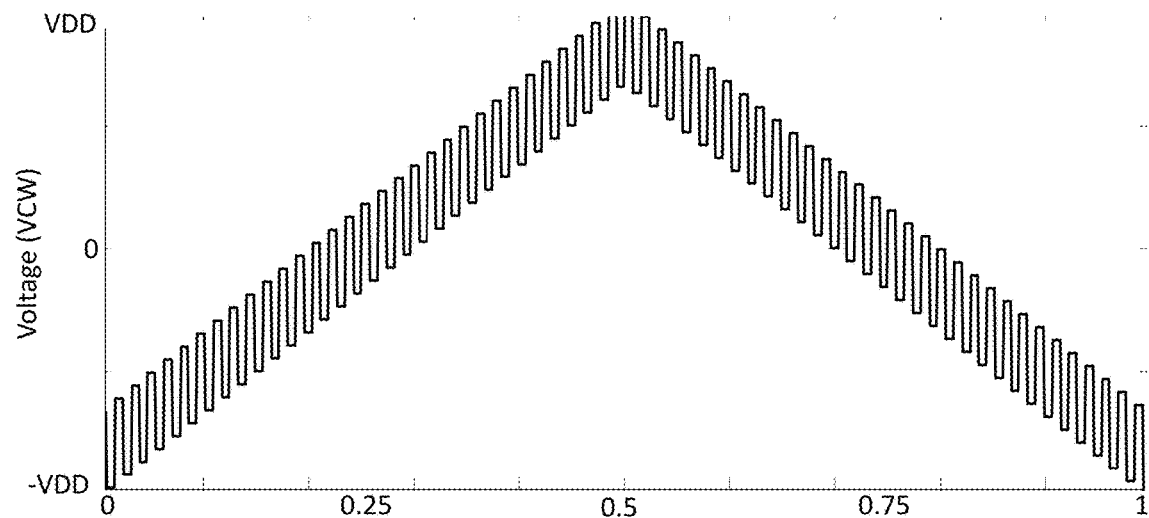
FIGS. 13 and 14 are graphs showing a square wave cyclic voltammetry regime for driving the cell 100 of the measurement circuit in FIG. 5 according to embodiments of the present disclosure.
Figure 14:
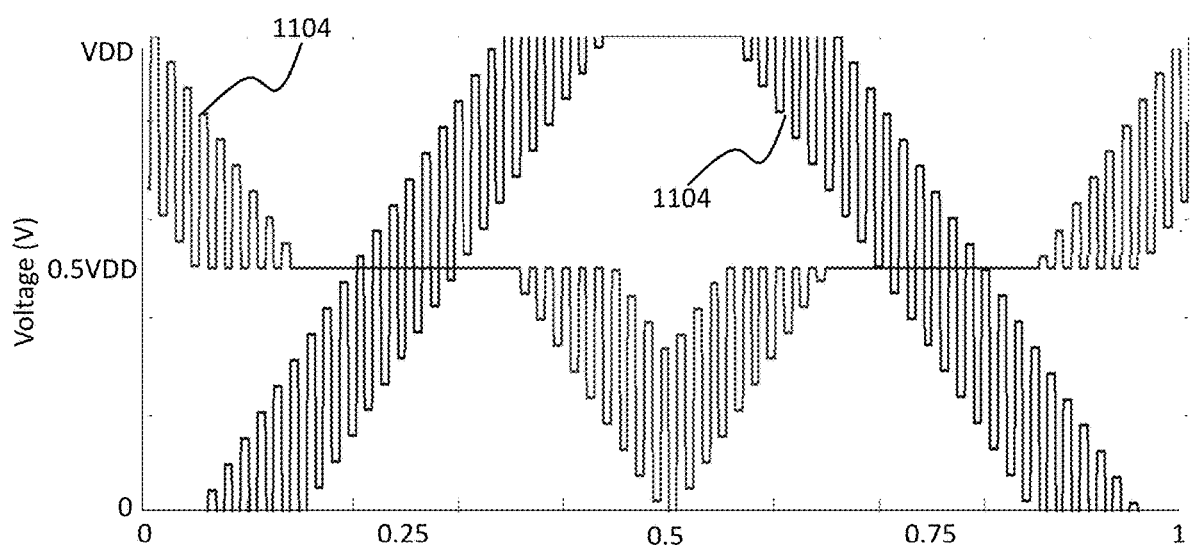

FIGS. 13 and 14 graphically illustrate an example cyclic square wave voltammetry sweep of the voltage drop VCW across the cell 100 from −VDD to +VDD and back to −VDD (FIG. 13) and the corresponding voltage at the counter electrode CE and working electrode WE as controlled by the control module 502 (FIG. 14). It can be seen that a bipolar voltage swing VCW is provided across the cell 100 over time, with a single unipolar supply voltage VDD. Control of the counter and working electrode voltages VCE, VWE is similar to that described with reference to FIG. 9, apart from them being modulated by a square wave during periods of respective voltage change.

As noted above with reference to FIG. 5, the output voltage VO of the second amplifier 204 may be expressed in terms of the bias voltage VWE of the working electrode WE, the current IWE measured by the second amplifier 204, and the feedback resistor RF of the second amplifier 204:

$$V_O = V_{WE} + I_{WE} R_F$$

In a practical implementation of the circuit 500, however, as the working electrode voltage VWE is raised or lowered, there will be a loss in headroom in the output voltage swing of the output voltage VO which may lead to clipping if not addressed.

To avoid clipping, the circuit 500 may be designed so as to prevent the output voltage VO from exceeding VDD−VH or falling below VH, where VH is the headroom voltage. In some embodiments, this may be achieved by varying the value of the feedback resistance RF as a function of the working electrode voltage VWE. Such control of the feedback resistance RF may be performed by the control module 502 or another module (not shown).

It will be appreciated that a reduction in the value of the feedback resistor RF will lead to a reduction in gain of the second amplifier 204. As such, the effective signal-to-noise ratio (SNR) of the output signal VO will also be reduced. To reduce the impact of noise, the sampling rate and/or the averaging of the ADC 206 may be increased to compensate for the reduced SNR.

The above implementation may be effective where the feedback resistor RF is provided in the feedback path in isolation of other components. It will be appreciated, however, that in some implementations a feedback capacitor (not shown) may be provided in the feedback path of the second amplifier 204 in parallel with the feedback resistor RF. In such embodiments, the complexity of the relationship between the feedback resistance RF, the working electrode voltage VWE and the output voltage VO is increased.

As such, in an alternative approach, to avoid clipping of the output voltage VO by the second amplifier 204, an offset current may be introduced into a virtual earth of the second amplifier 204.

Figure 15:
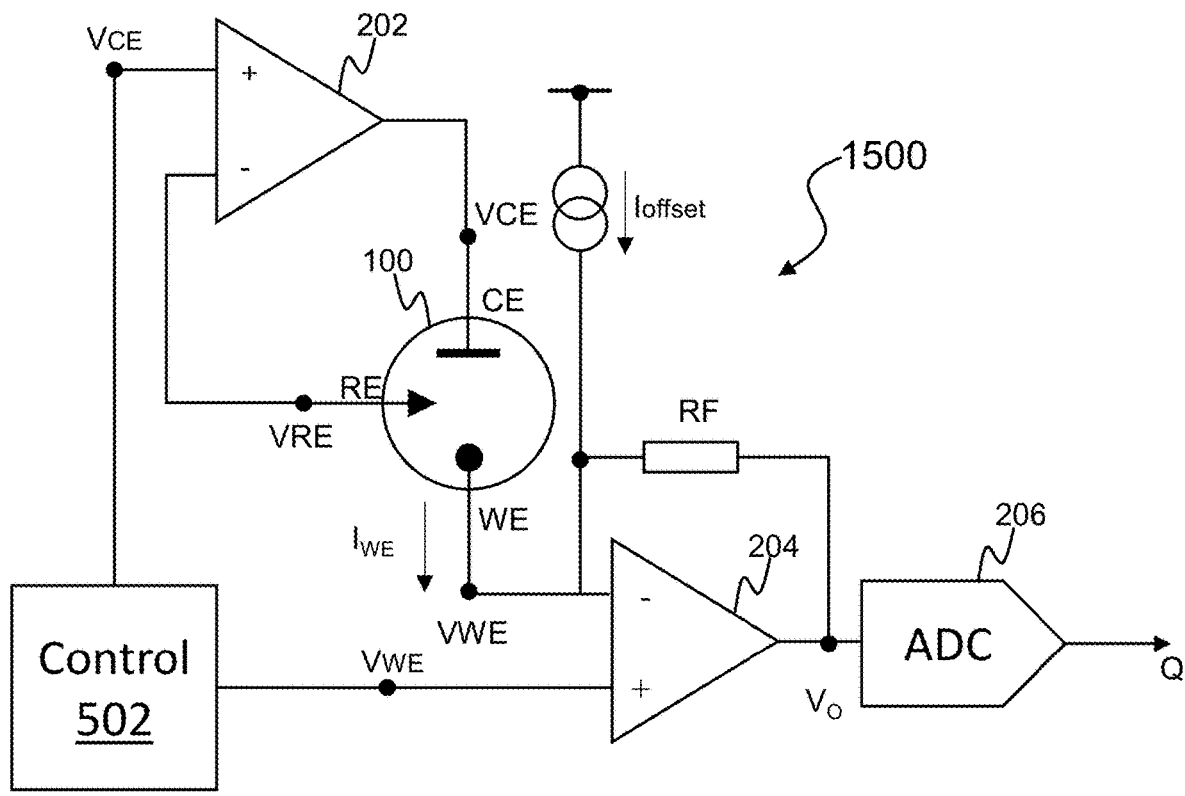
FIG. 15 is a schematic diagram of a variation of the drive and measurement circuit of FIG. 5.

FIG. 15 shows an example implementation 1500 of this approach based on the circuit 500 shown in FIG. 5, line parts having been given like numbering. In addition to all of the elements of the circuit 500 shown in FIG. 5, the circuit 1500 of FIG. 15 comprises a current source 1502 configured to inject an offset current Ioffset into the inverting input of the second amplifier 204. The output voltage VO may be given by the following expression.

$$V_O = V_{WE} + I_{WE} R_F - I_{offset} R_F$$

The injected offset current Ioffset may be adjusted based on the working electrode voltage VWE. For example, the offset current Ioffset may be set to bias the output voltage VO of the second amplifier 204 at VDD/2, i.e.:

$$I_{offset} = \frac{V_{WE} + V_{DD}/2}{R_F}$$

Under this condition, the output voltage VO may be defined as follows.

$$V_O = \frac{V_{DD}}{2} + I_{WE} R_F$$

It will be appreciated that in some implementations, headroom may not be an issue. If this is the case, then any offset could be removed digitally after conversion of the output voltage VO into the digital representation Q by the ADC 206.

Embodiments are described above with reference to a three-electrode cell 100 comprising a counter electrode CE, a working electrode WE and a reference electrode RE. Embodiments of the disclosure are not, however, limited to having three-electrodes. The concepts described herein are equally applicable to two-electrode cells. In particular, in any of the embodiments described above, the three-electrode cell 100 may be replaced with a two-electrode cell.

Figure 16:
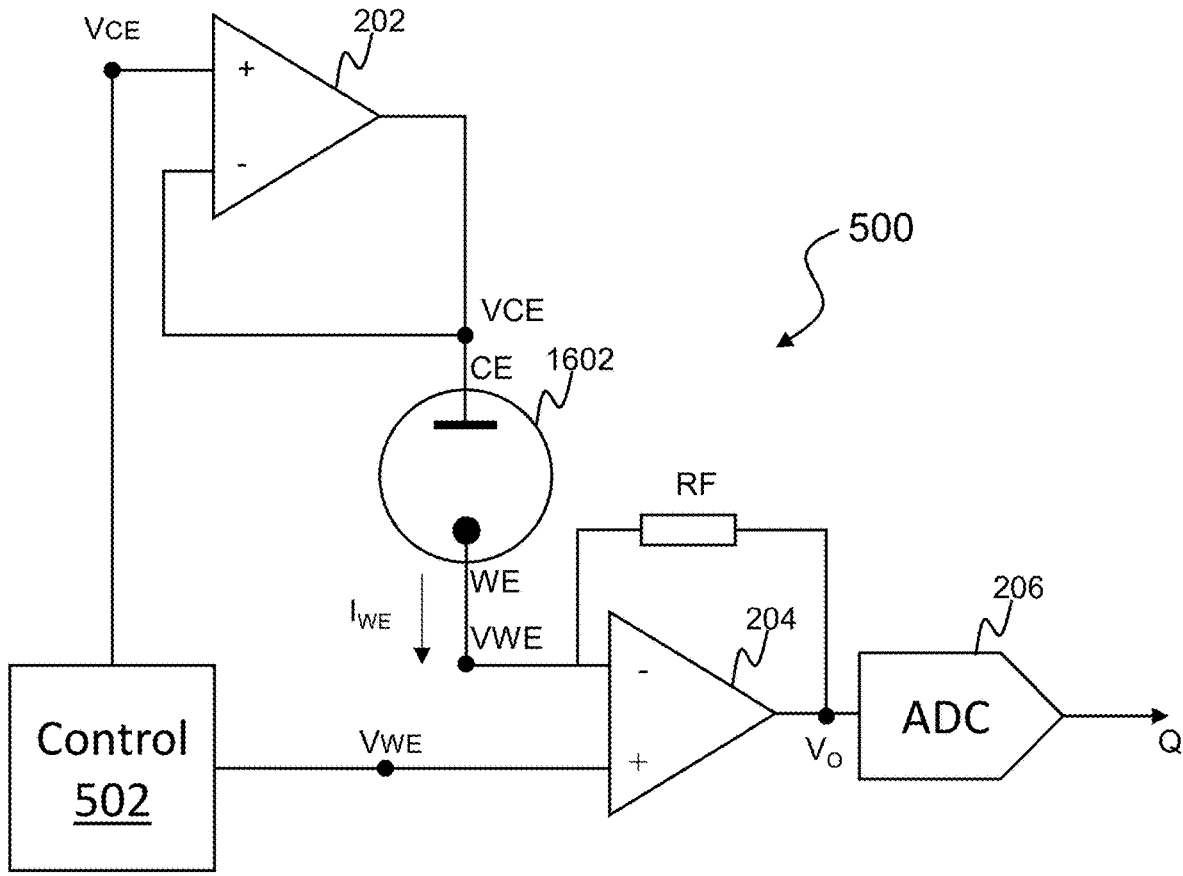
FIG. 16 is a schematic diagram of a variation of the drive and measurement circuit of FIG. 5, the three-electrode cell having been replaced with a two-electrode cell.

FIG. 16 is an example circuit 1600 which is a variation of the circuit 500 shown in FIG. 5, like parts having been given like numbering. In the circuit 1600, the cell 100 has been replaced with a two-electrode cell 1602. The counter electrode CE of the cell 1602 is coupled to the output of the first amplifier 202. The working electrode of the cell 1602 is coupled to the inverting input of the second amplifier 204. The inverting input of the first amplifier 202 is coupled to the counter electrode CE of the cell 1602. This is in contrast to the arrangement in FIG. 5 in which the inverting input of the first amplifier 202 is coupled to the reference electrode RE of the cell 1602.

Multiple Working Electrodes or Counter Electrodes

Embodiments are described above with reference to cells 100, 1600 comprising a single counter electrode CE and a single a working electrode WE. Embodiments of the disclosure are not, however, limited to having cells having only one counter electrode or only one working electrode. The concepts described herein are equally applicable to cells comprising multiple working electrodes or multiple counter electrodes. In doing so, such sensors may either providing redundancy or enabling the sensing of multiple analytes in a single chip. This may be particularly advantageous in applications such as continuous glucose monitoring, where it may be desirable to measure concentrations of several analytes including but not limited to two or more of glucose, ketones, oxygen, lactate, and the like.

Figures 17, 18:
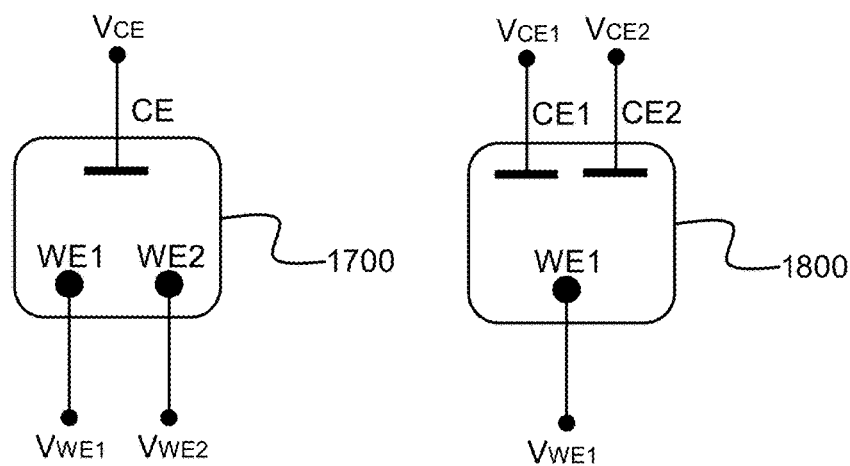
FIG. 17 is a schematic diagram of an electrochemical cell with one counter electrode and two working electrodes.
FIG. 18 is a schematic diagram of an electrochemical cell with one working electrode and two counter electrodes.

FIG. 17 illustrates an example electrochemical cell 1700 comprising first and second working electrode WE1, WE2 and a counter electrode CE. FIG. 18 illustrates an example electrochemical cell 1800 comprising first and second counter electrode CE1, CE2 and a single working electrode WE.

Figure 19:
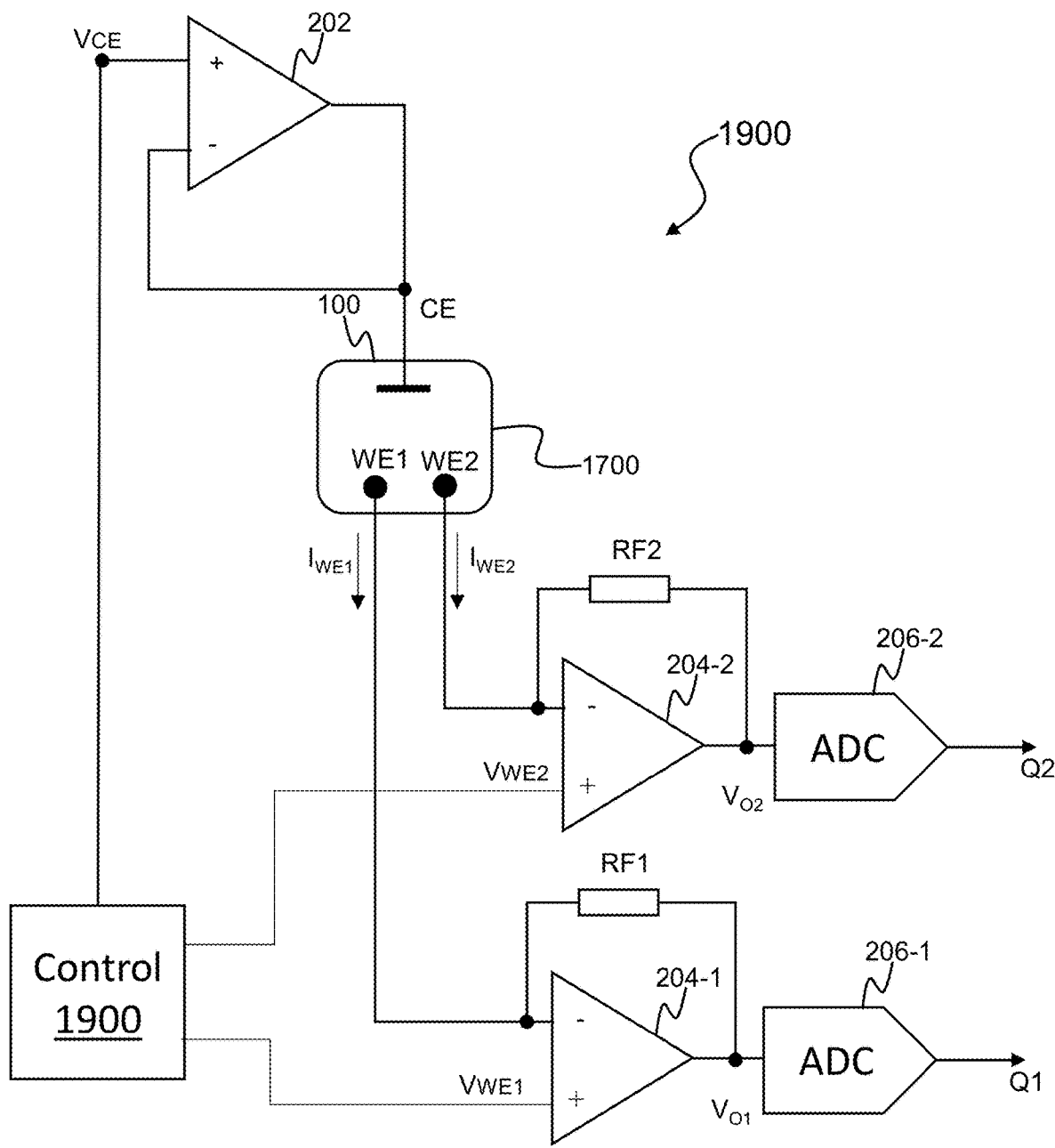
FIG. 19 is a schematic diagram of an example drive and measurement circuit for use with the cell shown in FIG. 17.

FIG. 19 illustrates an example drive and measurement circuit 1900 which is a variation of the circuit 1600 shown in FIG. 16, like parts having been denoted like numbering. The control module 500 has been replaced with a control module 1900. The single second amplifier 204 and ADC 206 have been replaced with first and second stage amplifiers 204-1, 204-2 and first and second ADCs 206-1, 206-2 arranged in a similar fashion to the second amplifier 204 and ADC 206 of the circuit 1600. The inverting input of the first stage amplifier 204-1 is coupled to the first working electrode WE1 of the cell 1700. The inverting input of the second stage amplifier 204-2 is coupled to the second working electrode WE2 of the cell 1700. The control module 1900 is configured to output a first working electrode bias voltage VWE1 to the non-inverting input of the first stage amplifier 204-1 and a second working electrode bias voltage to the non-inverting input of the second stage amplifier 204-2. The control module 1900 may thus be configured to independently control the counter electrode voltage VCE, the first working electrode voltage VWE1, and the second working electrode voltage VWE2.

The provision of two working electrodes WE1, WE2 enables the circuit 1900 to monitor two analytes by operating at two different DC operating conditions, i.e. providing a first bias voltage VCW1 between the counter electrode CE and the first working electrode WE1, and a second vias voltage VCW2 different to the first bias voltage VCW2 between the counter electrode CE and the second working electrode WE2.

By adjusting the counter electrode voltage VCE, the first working electrode voltage VWE1 and the second working electrode voltage VWE2, any combination of voltages may be achieved, provided:

$$j \vee \square\square\square \Sigma_j |V_{CWj}| < V_{DD}, V_{1,2} |V_{CW1}| \neq |V_{CW2}|$$

That is to say, the sum of the absolute of the distinct values of the voltages VCW1, VCW2 applied across the cell between each of the working electrodes WE1, WE2 and the counter electrode CE must be less than the supply voltage VDD. Given the above equation, it follows that:

$$V_{CE} = \frac{V_{DD}}{2} + \sum_j V_{CWj}$$

$$V_{WE1} = V_{CW1} - V_{CE}$$

$$V_{WE2} = V_{CW2} - V_{CE}$$

Figure 20:
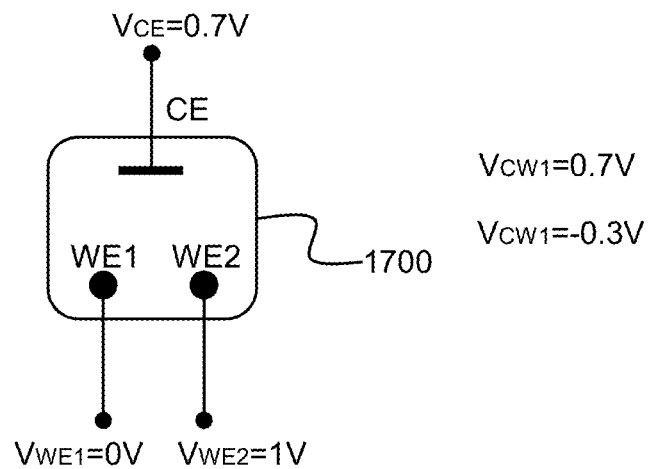
FIGS. 20 and 21 are worked examples of voltages applied at various electrodes of the electrochemical cell of FIG. 17.
Figure 21:
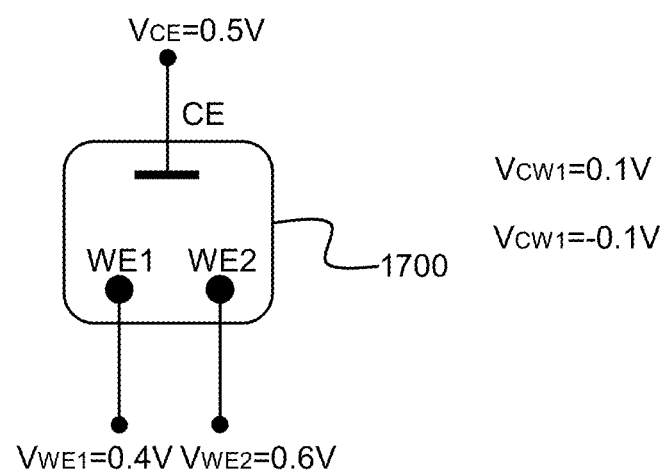

FIGS. 20 and 21 illustrate some worked examples of the above. It can be seen that the cell 1700 can operate with a positive bias between the counter electrode CE and the first working electrode WE1 and a negative bias between the counter electrode and the second working electrode WE2.

It will be appreciated that, whilst the embodiment described comprises two working electrodes WE1, WE2, in other embodiments three or more counter electrodes may be provided. The above condition can be extrapolated to any number of working electrodes, for example three working electrodes or four working electrodes. An equivalent condition also exists for cells comprising multiple counter electrodes and a single working electrode, such as that shown in FIG. 18.

The skilled person will recognise that some aspects of the above-described apparatus and methods may be embodied as processor control code, for example on a non-volatile carrier medium such as a disk, CD- or DVD-ROM, programmed memory such as read only memory (Firmware), or on a data carrier such as an optical or electrical signal carrier. For many applications embodiments of the invention will be implemented on a DSP (Digital Signal Processor), ASIC (Application Specific Integrated Circuit) or FPGA (Field Programmable Gate Array). Thus the code may comprise conventional program code or microcode or, for example code for setting up or controlling an ASIC or FPGA. The code may also comprise code for dynamically configuring re-configurable apparatus such as re-programmable logic gate arrays. Similarly the code may comprise code for a hardware description language such as Verilog™ or VHDL (Very high-speed integrated circuit Hardware Description Language). As the skilled person will appreciate, the code may be distributed between a plurality of coupled components in communication with one another. Where appropriate, the embodiments may also be implemented using code running on a field-(re)programmable analogue array or similar device in order to configure analogue hardware.

Note that as used herein the term module shall be used to refer to a functional unit or block which may be implemented at least partly by dedicated hardware components such as custom defined circuitry and/or at least partly be implemented by one or more software processors or appropriate code running on a suitable general-purpose processor or the like. A module may itself comprise other modules or functional units. A module may be provided by multiple components or sub-modules which need not be co-located and could be provided on different integrated circuits and/or running on different processors.

Embodiments may be implemented in a host device, especially a portable and/or battery powered host device such as a mobile computing device for example a laptop or tablet computer, a games console, a remote control device, a home automation controller or a domestic appliance including a domestic temperature or lighting control system, a toy, a machine such as a robot, an audio player, a video player, or a mobile telephone for example a smartphone.

It should be noted that the above-mentioned embodiments illustrate rather than limit the invention, and that those skilled in the art will be able to design many alternative embodiments without departing from the scope of the appended claims. The word "comprising" does not exclude the presence of elements or steps other than those listed in a claim, "a" or "an" does not exclude a plurality, and a single feature or other unit may fulfil the functions of several units recited in the claims. Any reference numerals or labels in the claims shall not be construed so as to limit their scope.

As used herein, when two or more elements are referred to as "coupled" to one another, such term indicates that such two or more elements are in electronic communication or mechanical communication, as applicable, whether connected indirectly or directly, with or without intervening elements.

This disclosure encompasses all changes, substitutions, variations, alterations, and modifications to the example embodiments herein that a person having ordinary skill in the art would comprehend. Similarly, where appropriate, the appended claims encompass all changes, substitutions, variations, alterations, and modifications to the example embodiments herein that a person having ordinary skill in the art would comprehend. Moreover, reference in the appended claims to an apparatus or system or a component of an apparatus or system being adapted to, arranged to, capable of, configured to, enabled to, operable to, or operative to perform a particular function encompasses that apparatus, system, or component, whether or not it or that particular function is activated, turned on, or unlocked, as long as that apparatus, system, or component is so adapted, arranged, capable, configured, enabled, operable, or operative. Accordingly, modifications, additions, or omissions may be made to the systems, apparatuses, and methods described herein without departing from the scope of the disclosure. For example, the components of the systems and apparatuses may be integrated or separated. Moreover, the operations of the systems and apparatuses disclosed herein may be performed by more, fewer, or other components and the methods described may include more, fewer, or other steps. Additionally, steps may be performed in any suitable order. As used in this document, "each" refers to each member of a set or each member of a subset of a set.

Although exemplary embodiments are illustrated in the figures and described below, the principles of the present disclosure may be implemented using any number of techniques, whether currently known or not. The present disclosure should in no way be limited to the exemplary implementations and techniques illustrated in the drawings and described above.

Unless otherwise specifically noted, articles depicted in the drawings are not necessarily drawn to scale.

All examples and conditional language recited herein are intended for pedagogical objects to aid the reader in understanding the disclosure and the concepts contributed by the inventor to furthering the art, and are construed as being without limitation to such specifically recited examples and conditions. Although embodiments of the present disclosure have been described in detail, it should be understood that various changes, substitutions, and alterations could be made hereto without departing from the spirit and scope of the disclosure.

Although specific advantages have been enumerated above, various embodiments may include some, none, or all of the enumerated advantages. Additionally, other technical advantages may become readily apparent to one of ordinary skill in the art after review of the foregoing figures and description.

To aid the Patent Office and any readers of any patent issued on this application in interpreting the claims appended hereto, applicants wish to note that they do not intend any of the appended claims or claim elements to invoke 35 U.S.C. § 112(f) unless the words "means for" or "step for" are explicitly used in the particular claim.

The invention claimed is:

1. Circuitry for measuring a characteristic of an electrochemical cell, the electrochemical cell comprising at least one working electrode and a counter electrode, the circuitry comprising:
   driver circuitry configured to apply a working bias voltage to the at least one working electrode and a counter bias voltage at the counter electrode to produce a first voltage bias between the at least one working electrode and the counter electrode;
   control circuitry configured to adjust the first voltage bias over a first bias range by varying the working bias voltage and the counter bias voltage.

2. Circuitry of claim 1, wherein the control circuitry is configured to hold the working bias voltage at a fixed midpoint voltage while varying the counter bias voltage between a lower reference voltage and an upper reference voltage of the driver circuitry.

3. Circuitry of claim 2, wherein the lower reference voltage is a ground reference voltage of the driver circuitry positively offset by a headroom voltage, and wherein the upper reference voltage is a supply voltage of the driver circuitry negatively offset by the headroom voltage.

4. Circuitry of claim 2, wherein when the first voltage bias is a negative voltage bias, the control circuitry is configured to increase a magnitude of the negative voltage bias by decreasing the counter bias voltage until the counter bias voltage is substantially equal to the lower reference voltage.

5. Circuitry of claim 4, wherein, when the counter bias voltage reaches the lower reference voltage, the control circuitry is configured to increase the working bias voltage to further increase the magnitude of the negative voltage bias.

6. Circuitry of claim 2, wherein when the first voltage bias is a positive voltage bias, the control circuitry is configured to increase a magnitude of the positive voltage bias by increasing the counter bias voltage until the counter bias voltage is substantially equal to the upper reference voltage.

7. Circuitry of claim 6, wherein, when the counter bias voltage reaches the upper reference voltage, the control circuitry is configured to decrease the working bias voltage to further increase the magnitude of the positive voltage bias.

8. Circuitry of claim 1, wherein the first bias range is between a negative bias voltage and a positive bias voltage.

9. Circuitry of claim 1, wherein:
during a first time period, the control circuitry is configured to linearly increase the first voltage bias from the negative bias voltage to the positive bias voltage; and
during a second time period, the control circuitry is configured to linearly decrease the first voltage bias from the positive bias voltage to the negative bias voltage.

10. Circuitry of claim 1, wherein the first voltage bias is modulated by a square wave.

11. Circuitry of claim 10, wherein the voltage bias is modulated by modulating the working bias voltage and/or the counter bias voltage.

12. Circuitry of claim 1, comprising:
a transimpedance amplifier (TIA) comprising:
a first input coupled to the working electrode;
a second input configured to receive the working bias voltage;
an output configured to output an output voltage; and
a feedback resistor coupled between the output and the first input.

13. Circuitry of claim 12, wherein the control circuitry is configured to vary a resistance of the feedback resistor in dependence the working bias voltage.

14. Circuitry of claim 13, comprising a current source configured to provide an offset current to the first input.

15. Circuitry of claim 12, further comprising an analog-to-digital converter configured to convert the output voltage into a digital representation of the output voltage.

16. Circuitry of claim 1, wherein the at least one working electrode comprises a first working electrode and a second working electrode.

17. Circuitry of claim 16, wherein:
the working bias voltage is applied to the first working electrode;
the first voltage bias is between the first working electrode and the counter electrode;
the driver circuitry is configured to apply a second working bias voltage to the second working electrode to produce a second voltage bias between the second working electrode and the counter electrode; and
the control circuitry is configured to adjust the second voltage bias over a second bias range by varying the second working bias voltage and the counter bias voltage.

18. Circuitry of claim 17, wherein the control circuitry is configured to adjust the working bias voltage, the second working bias voltage and the counter bias voltage such that a sum of absolute values of the first voltage bias and the second voltage vias is less than a supply voltage of the driver circuitry.

19. An electronic device, comprising the circuitry of claim 1.

20. The electronic device of claim 19, wherein the device comprises one of a continuous glucose monitor, a mobile computing device, a laptop computer, a tablet computer, a games console, a remote control device, a home automation controller or a domestic appliance, a toy, a robot, an audio player, a video player, or a mobile telephone, and a smartphone.

* * * * *